United States Patent
Schoeneweiss et al.

(10) Patent No.: US 9,325,026 B2
(45) Date of Patent: *Apr. 26, 2016

(54) CO(II)TETRAMETHOXYPHENYLPORPHYRIN ADDITIVE TO PFSA PEMS FOR IMPROVED FUEL CELL DURABILITY

(71) Applicant: GM GLOBAL TECHNOLOGY OPERATIONS LLC, Detroit, MI (US)

(72) Inventors: Michael R. Schoeneweiss, West Henrietta, NY (US); Timothy J. Fuller, Pittsford, NY (US); Frank Coms, Fairport, NY (US); Sean M. MacKinnon, Montreal (CA)

(73) Assignee: GM Global Technology Operations LLC, Detroit, MI (US)

( * ) Notice: Subject to any disclaimer, the term of this patent is extended or adjusted under 35 U.S.C. 154(b) by 349 days.

This patent is subject to a terminal disclaimer.

(21) Appl. No.: 13/852,674

(22) Filed: Mar. 28, 2013

(65) Prior Publication Data

US 2013/0288158 A1 Oct. 31, 2013

Related U.S. Application Data

(62) Division of application No. 12/551,284, filed on Aug. 31, 2009, now Pat. No. 8,409,765.

(51) Int. Cl.
*H01M 8/10* (2006.01)
*C07D 487/22* (2006.01)
*C08J 5/22* (2006.01)

(52) U.S. Cl.
CPC ........... *H01M 8/1039* (2013.01); *C07D 487/22* (2013.01); *C08J 5/2237* (2013.01); *H01M 8/1023* (2013.01); *H01M 8/1048* (2013.01); *B01D 2323/385* (2013.01); *C08J 2327/18* (2013.01); *H01M 2008/1095* (2013.01); *H01M 2300/0082* (2013.01); *Y02E 60/521* (2013.01)

(58) Field of Classification Search
CPC ............ H01M 8/1039; H01M 8/1048; H01M 2008/1095; H01M 2300/0082; Y02E 60/521; C07D 487/22; C08J 5/2237
See application file for complete search history.

(56) References Cited

U.S. PATENT DOCUMENTS

| | | | |
|---|---|---|---|
| 5,006,408 A | 4/1991 | Green et al. | |
| 5,021,602 A | 6/1991 | Clement et al. | |
| 5,037,917 A | 8/1991 | Babb et al. | |
| 5,066,746 A | 11/1991 | Clement et al. | |
| 5,159,037 A | 10/1992 | Clement et al. | |
| 5,159,038 A | 10/1992 | Babb et al. | |
| 5,741,611 A | 4/1998 | Fleischer et al. | |
| 5,910,378 A | 6/1999 | Debe et al. | |
| 6,124,060 A | 9/2000 | Akita et al. | |
| 6,183,668 B1 | 2/2001 | Debe et al. | |
| 6,277,512 B1 | 8/2001 | Hamrock et al. | |
| 6,444,343 B1 | 9/2002 | Prakash et al. | |
| 6,523,699 B1 | 2/2003 | Akita et al. | |
| 6,559,237 B1 | 5/2003 | Mao et al. | |
| 6,847,518 B2 | 1/2005 | Fukuda et al. | |
| 6,875,537 B2 | 4/2005 | Tani et al. | |
| 6,926,984 B2 | 8/2005 | Asano et al. | |
| 6,933,068 B2 | 8/2005 | Asano et al. | |
| 6,953,653 B2 | 10/2005 | Smith et al. | |
| 6,986,962 B2 | 1/2006 | Oyanagi et al. | |
| 7,001,929 B2 | 2/2006 | Goto et al. | |
| 7,045,241 B2 | 5/2006 | Akita et al. | |
| 8,409,765 B2 * | 4/2013 | Schoeneweiss et al. | 429/492 |
| 8,735,021 B2 * | 5/2014 | Fuller et al. | 429/492 |
| 2001/0018144 A1 | 8/2001 | Watakabe et al. | |
| 2002/0014405 A1 | 2/2002 | Arcella et al. | |
| 2003/0017379 A1 | 1/2003 | Menashi | |
| 2004/0214058 A1 | 10/2004 | Tada et al. | |
| 2004/0214065 A1 | 10/2004 | Kanaoka et al. | |
| 2005/0014927 A1 | 1/2005 | Akita | |
| 2005/0043487 A1 | 2/2005 | Felix et al. | |
| 2005/0048342 A1 | 3/2005 | Wakahoi et al. | |
| 2005/0053810 A1 | 3/2005 | Kato et al. | |
| 2005/0058864 A1 | 3/2005 | Goebel | |
| 2005/0064260 A1 | 3/2005 | Otsuki et al. | |
| 2005/0100770 A1 | 5/2005 | Sugawara et al. | |
| 2005/0106440 A1 | 5/2005 | Komiya | |
| 2005/0116206 A1 | 6/2005 | Kakuta et al. | |
| 2005/0130024 A1 | 6/2005 | Otsuki et al. | |
| 2005/0142397 A1 | 6/2005 | Wakahoi et al. | |
| 2005/0143530 A1 | 6/2005 | Iwadate et al. | |

(Continued)

FOREIGN PATENT DOCUMENTS

| | | |
|---|---|---|
| DE | 69701550 T2 | 1/2001 |
| DE | 112009002507 T5 | 1/2012 |
| JP | 2003535929 | 12/2003 |
| JP | 2005-105176 | 4/2005 |
| JP | 2005129298 A | 5/2005 |
| JP | 2005166557 A | 6/2005 |
| JP | 2005179380 A | 7/2005 |
| JP | 2009 249 487 A | 10/2009 |
| WO | 98/42037 A1 | 9/1998 |
| WO | 2004/051776 | 6/2004 |
| WO | 2005/060039 A1 | 6/2005 |
| WO | 2007/052954 A1 | 5/2007 |
| WO | 2007/144633 A1 | 12/2007 |

OTHER PUBLICATIONS

Smith, D.W. et al., "Perfluorocyclobutane Aromatic Polyethers. Synthesis and Characterization of New Siloxane-Containing Fluoropolymers," Macromolecules 1996, v. 29, pp. 852-860.

Smith, D.W. et al., "Perfluorocyclobutane (PFCB) polyaryl ethers: versatile coatings material," J. of Fluorine Chem., v. 104, pp. 109-117 (2000).

(Continued)

*Primary Examiner* — Laura Weiner
(74) *Attorney, Agent, or Firm* — Brooks Kushman P.C.

(57) ABSTRACT

An ion conducting membrane for fuel cell applications includes an ion conducting polymer and a porphyrin-containing compound at least partially dispersed within the ion conducting polymer. The ion conducting membranes exhibit improved performance over membranes not incorporating such porphyrin-containing compounds.

4 Claims, 3 Drawing Sheets

(56) References Cited

U.S. PATENT DOCUMENTS

| | | |
|---|---|---|
| 2005/0170252 A1 | 8/2005 | Aihara |
| 2005/0175886 A1 | 8/2005 | Fukuda et al. |
| 2005/0197467 A1 | 9/2005 | Komiya et al. |
| 2005/0227138 A1 | 10/2005 | Fukuda et al. |
| 2005/0233181 A1 | 10/2005 | Wariishi et al. |
| 2005/0260474 A1 | 11/2005 | Asano et al. |
| 2006/0019147 A1 | 1/2006 | Fukuda et al. |
| 2006/0127728 A1 | 6/2006 | Otsuki et al. |
| 2006/0177719 A1 | 8/2006 | Fuller et al. |
| 2007/0042242 A1 | 2/2007 | Tada et al. |
| 2007/0099054 A1 | 5/2007 | Fuller et al. |
| 2007/0141237 A1 | 6/2007 | Okiyama et al. |
| 2008/0027152 A1 | 1/2008 | Maier et al. |
| 2009/0278083 A1 | 11/2009 | Fuller et al. |
| 2009/0278091 A1 | 11/2009 | MacKinnon et al. |
| 2009/0281245 A1 | 11/2009 | MacKinnon et al. |
| 2009/0281262 A1 | 11/2009 | MacKinnon et al. |
| 2009/0281270 A1 | 11/2009 | Fuller et al. |
| 2011/0287335 A1 | 11/2011 | Akita et al. |

OTHER PUBLICATIONS

Souzy, R. et al., "Functional fluoropolymers for fuel cell membranes," Solid State Ionics, v. 176, pp. 2839-2848 (2005).

Souzy, R. et al., "Functional fluoropolymers for fuel cell membranes," Prog. Polm. Sci. 30, 2005, pp. 644-687.

"Fluorel Technical Data Sheets," MatWeb Material Property Data website, http://www.matweb.com/search/GetMatIsByTradename.aspx?navletter=F&tn=Fluorel%E2%84%A2.

Nafion perfluorinated resin, Sigma-Aldrich Online Catalog, http://www.sigmaaldrich.com/catalog/ProductDetail.do?lang=en&N4=495786|ALDRICH&N5=SEARCH_CONCAT_PNO|BRAND_KEY&F=SPEC.

Ford, L.A. et al., "New Aromatic Perfluorovinyl Ether Monomers Containing the Sulfonimide Acid Functionality," Polymeric Materials Science & Eng., v. 83, 2000, pp. 10-11 (American Chemical Society).

Souzy, R. et al., "Synthesis and (co)polymerization of monofluoro, difluoro, trifluorostyrene and ((trifluorovinyl)oxy) benzene," Prog. Polm. Sci. 29 (2004), pp. 75-106.

\* cited by examiner

CO(II)TETRAMETHOXYPHENYLPORPHYRIN ADDITIVE TO PFSA PEMS FOR IMPROVED FUEL CELL DURABILITY

This application is a division of U.S. application Ser. No. 12/551,284 filed Aug. 31, 2009, now U.S. Pat. No. 8,409,765 issued Apr. 2, 2013, the disclosure of which is incorporated in its entirety by reference herein.

TECHNICAL FIELD

The present invention relates to ion conducting membranes for fuel cell applications.

BACKGROUND

Fuel cells are used as an electrical power source in many applications. In particular, fuel cells are proposed for use in automobiles to replace internal combustion engines. A commonly used fuel cell design uses a solid polymer electrolyte ("SPE") membrane or proton exchange membrane ("PEM") to provide ion transport between the anode and cathode.

In proton exchange membrane type fuel cells, hydrogen is supplied to the anode as fuel and oxygen is supplied to the cathode as the oxidant. The oxygen can either be in pure form ($O_2$) or air (a mixture of $O_2$ and $N_2$). PEM fuel cells typically have a membrane electrode assembly ("MEA") in which a solid polymer membrane has an anode catalyst on one face, and a cathode catalyst on the opposite face. The anode and cathode layers of a typical PEM fuel cell are formed of porous conductive materials, such as woven graphite, graphitized sheets, or carbon paper to enable the fuel to disperse over the surface of the membrane facing the fuel supply electrode. Each electrode has finely divided catalyst particles (for example, platinum particles), supported on carbon particles, to promote oxidation of hydrogen at the anode and reduction of oxygen at the cathode. Protons flow from the anode through the ion conductive polymer membrane to the cathode where they combine with oxygen to form water which is discharged from the cell. Typically, the ion conductive polymer membrane includes a perfluorinated sulfonic acid (PFSA) ionomer.

The MEA is sandwiched between a pair of porous gas diffusion layers ("GDL"), which in turn are sandwiched between a pair of non-porous, electrically conductive elements or plates. The plates function as current collectors for the anode and the cathode, and contain appropriate channels and openings formed therein for distributing the fuel cell's gaseous reactants over the surface of respective anode and cathode catalysts. In order to produce electricity efficiently, the polymer electrolyte membrane of a PEM fuel cell must be thin, chemically stable, proton transmissive, non-electrically conductive and gas impermeable. In typical applications, fuel cells are provided in arrays of many individual fuel cell stacks in order to provide high levels of electrical power.

One mechanism by which ion conducting polymer membranes degrade is via loss of fluorine (i.e., fluoride emission) under open circuit voltage (OCV) and dry operating conditions at elevated temperatures. Additives to PFSA membranes are required to improve fuel cell life, increase membrane durability and reduce fluoride emissions under these conditions.

Accordingly, there is a need for improved ion conducting membranes with reduced fluoride emissions.

SUMMARY OF EXEMPLARY EMBODIMENTS OF THE INVENTION

The present invention solves one or more problems of the prior art by providing in at least one embodiment an ion conducting membrane for fuel cell applications. The ion conducting membrane of this embodiment includes an ion conducting polymer and a porphyrin-containing compound at least partially dispersed within the ion conducting polymer in a sufficient amount to reduce fluoride emissions from the membrane. Moreover, the incorporation of a porphyrin-containing compound advantageously increases membrane life while decreasing electrode voltage degradation in fuel cells operating at open circuit conditions at 95° C. and 50% relative humidity. Additional benefits include reduced cost compared with additives presently used to mitigate PFSA-fuel cell ion conducting membranes.

BRIEF DESCRIPTION OF THE DRAWINGS

Exemplary embodiments of the present invention will become more fully understood from the detailed description and the accompanying drawings, wherein.

DETAILED DESCRIPTION OF EXEMPLARY EMBODIMENTS

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

Figure 1:
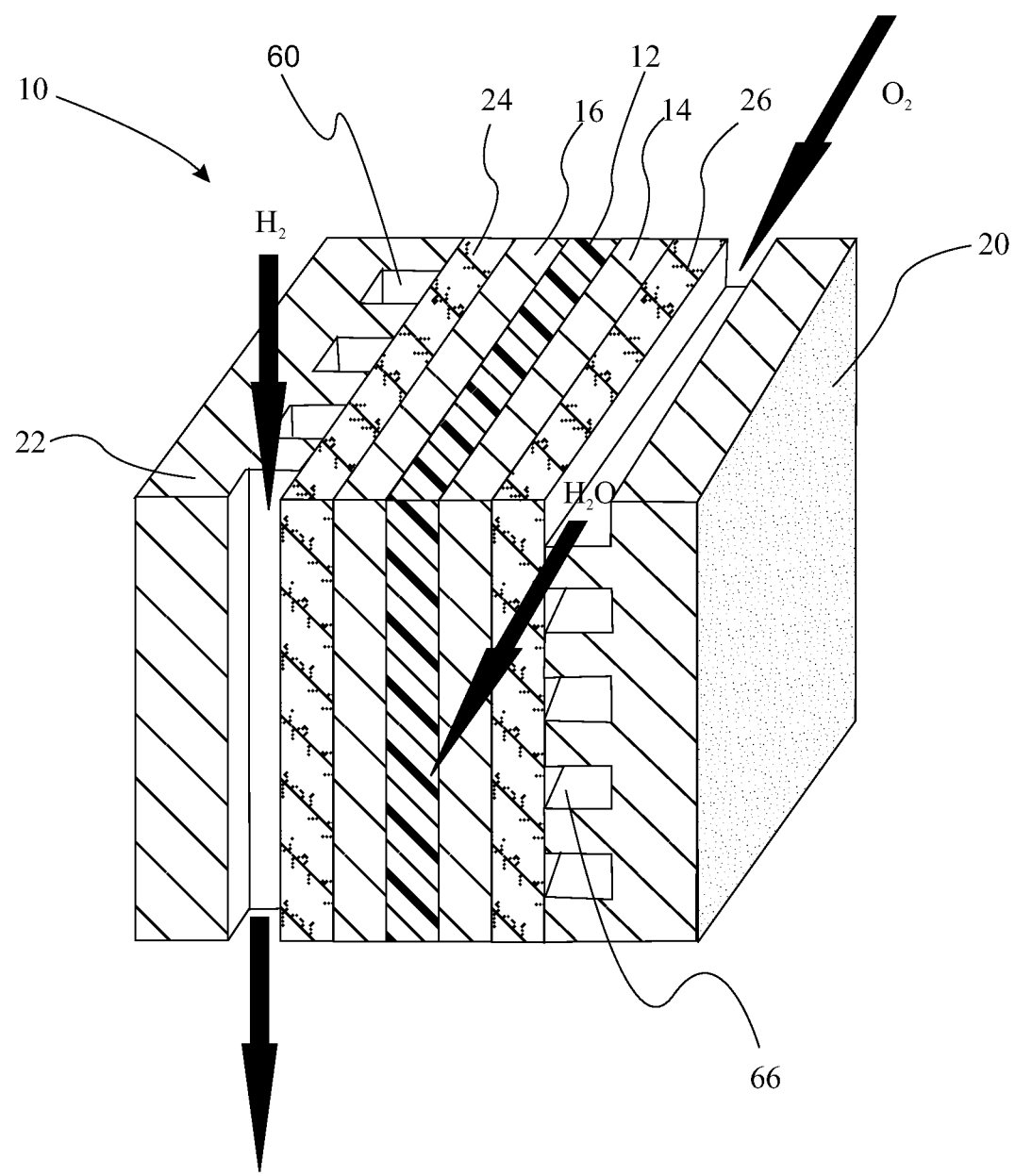
FIG. 1 is a schematic illustration of a fuel cell that incorporates an ion conducting membrane of one or more embodiments of the invention.

With reference to FIG. 1, a fuel cell that incorporates an ion conducting membrane of one or more embodiments of the invention is provided. PEM fuel cell 10 includes polymeric ion conductive membrane 12 disposed between cathode catalyst layer 14 and anode catalyst layer 16. Polymeric ion conductive membrane 12 includes an effective amount of stannate as set forth below. Fuel cell 10 also includes conductive plates 20, 22, gas channels 60 and 66, and gas diffusion layers 24 and 26.

In an embodiment of the present invention, an ion conducting membrane for fuel cell applications includes an ion conducting polymer and a porphyrin-containing compound at least partially dispersed within the ion conducting polymer. In a variation, the porphyrin-containing compound the porphyrin-containing compound includes a moiety having formula 1:

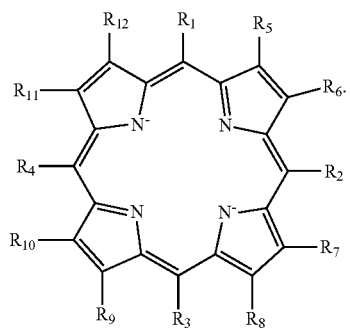

wherein:

$R_1$, $R_2$, $R_3$, $R_4$, $R_5$, $R_6$, $R_7$, $R_8$, $R_9$, $R_{10}$, $R_{11}$, $R_{12}$ are each independently hydrogen, alkyl, or aryl. In a refinement, $R_1$, $R_2$, $R_3$, $R_4$, are each independently substituted or unsubstituted alkyl or phenyl. In another refinement, $R_1$, $R_2$, $R_3$, $R_4$, are each phenylmethoxy. In still another refinement, $R_5$, $R_6$, $R_7$, $R_8$, $R_9$, $R_{10}$, $R_{11}$, $R_{12}$ are each hydrogen. In this context, substitutions may be with halogens, methoxy, ethoxy, and the like. In addition, in the case of aryl and phenyl, substitutions may also be with alkyl groups.

In another variation of the present embodiment, the porphyrin-containing compound is present in an amount from about 0.001 to about 50 weight percent of the total weight percent of the total weight of the ion conducting membrane. In a refinement, the porphyrin-containing compound is present in an amount from about 0.1 to about 10 weight percent of the total weight percent of the total weight of the ion conducting membrane.

In still another variation of the present embodiment, the porphyrin-containing compound has formula 2:

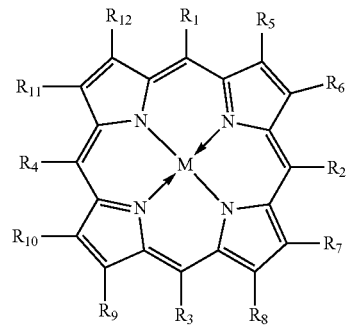

wherein M is a metal or metal-containing moiety. Examples of suitable metals for M or for inclusion, include but are not limited do in the metal containing moiety include Co, Fe, Mg, Mn, Cu, Ni, Pd, Ru, Vn, Zn, Al, B, Si, Al, In, Pb, Ag, Sn, Ti, V, Pt, Ce, and the like. Specific examples for M include $Co^{2+}$, $Co^{3+}$, $Fe^{2+}$, $Fe^{3+}$, $Mg^{1+}$, $Mg^{2+}$, $Mn^{1+}$, $Mn^{2+}$, $Mn^{3+}$, $ClMn^{3+}$, $HOMn^{3+}$, $Cu^{+1}$, $Cu^{2+}$, $Ni^{1+}$, $Ni^{2+}$, $Pd^{1+}$, $Pd^{2+}$, $Ru^{1+}$, $Ru^{2+}$, $Ru^{4+}$, $Vn^{4+}$, $Zn^{1+}$, $Zn^{2+}$, $Al^{3+}$, B, $Si(OH)_2^{2+}$, $Al^{3+}$, $HOIn^{3+}$, $HOIn^{3+}$, $Pb^{2+}$, $Ag^+$, $Sn^{2+}$, $Sn^{4+}$, $Ti^{3+}$, $Ti^{4+}$, $VO^+$, $Pt^{2+}$, $Ce^{3+}$, $Ce^{4+}$.

In another variation of the present embodiment, the ion-conducting membrane further comprises a metal-containing compound having a metal (i.e., metal ion) selected from the group consisting of Ce(III), Ce(IV), Mn(II) and Mn(IV). Examples of metal-containing compounds include $MnO_2$, $Mn_2O_3$, $MnCl_2$, $MnSO_4$, $CeCl_3$, $Ce_2(CO_3)_3$, $CeF_3$, $Ce_2O_3$, $CeO_2$, $Ce(SO_4)_2$) $Ce(OSO_2CF_3)_3$, and combinations thereof. In a further refinement, the metal-containing compound is selected from the group consisting of $MnO_2$, $Mn_2O_3$ $MnCl_2$, $MnSO_4$, and combinations thereof.

As set forth above, the membrane of the present invention includes an ion conducting polymer. Such polymers include sulfonated tetrafluoroethylene-based fluoropolymer-copolymers. Sometimes this class of polymers is referred to as perfluorosulfonic acid (PFSA) polymers. Specific examples of such polymers include the Nafion® line of polymers commercially available from E. I. du Pont de Nemours and Company. In another refinement, the ion conducting polymer comprises a perfluorocyclobutyl moiety. Examples of these suitable polymers are set forth in U.S. Pat. Nos. 3,282,875; 3,041,317; 3,718,627; 2,393,967; 2,559,752; 2,593,583; 3,770,567; 2,251,660; U.S. Pat. Pub. No. 20070099054; U.S. patent application Ser. No. 12/197,530 filed Aug. 25, 2008; Ser. No. 12/197,537 filed Aug. 25, 2008; Ser. No. 12/197,545 filed Aug. 25, 2008; and Ser. No. 12/197,704 filed Aug. 25, 2008; the entire disclosures of which are hereby incorporated by reference.

The following examples illustrate the various embodiments of the present invention. Those skilled in the art will recognize many variations that are within the spirit of the present invention and scope of the claims.

Membrane Preparation. Cobalt(II)tetramethoxyphenylporphyrin (CoTMPP) is added at 5 wt. % based on perfluorosulfonic acid (PFSA) polymer solids in 1-propanol and water (3/2 weight ratio) and is homogenized with an IKA homogenizer for about 4 minutes. The CoTMPP is soluble in the ionomer solution, which is centrifuged to remove suspended air bubbles. The blood-red supernate is coated on glass with an 8-mil coating gap, Bird applicator, and the resultant wet film is then heated at 80° C. for 1 h in air and then at 130° C. for 4 h under vacuum. The green film is floated off glass and air-dried to obtain a 16-um membrane.

Figure 2:
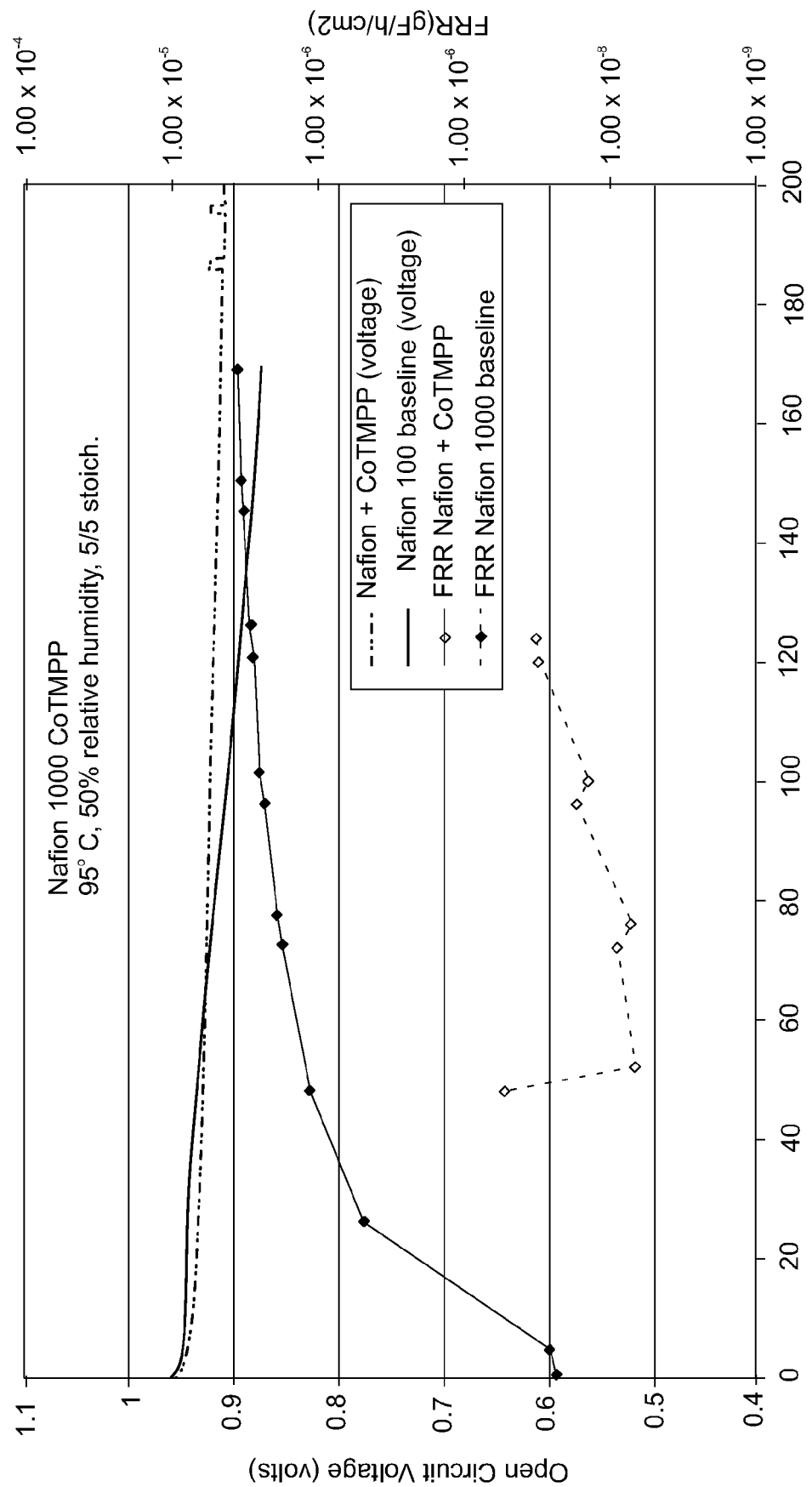
FIG. 2 provides plots of the cell voltage degradation and fluoride release rate (FRR) versus time for Nafion® 1000 membrane with and without Cobalt(II)tetramethoxyphenylporphyrin.

The improved chemical durability is measured under open circuit voltage (OCV) using 50-cm² membrane electrode assemblies that are sub-gasketed to 38-cm² active areas. The electrode is a platinum on carbon slurry coated on the microporous layer of a carbon fiber diffusion media to a 0.4 mg Pt cm$^{-2}$ loading on both the anode and cathode. The fuel cell, with a serpentine flow-field, is operated at 95° C. and at 50% inlet R.H at a 5/5 stoichiometry on the anode and cathode at a 0.2 A cm$^{-2}$ equivalent flow and 50 kPa gauge. The OCV is monitored for 200 to 800 hours and the fluoride release rate (FRR) is measured from the analysis of outlet water to determine the percent loss of fluorine versus the total fluorine inventory of the membrane. The improved chemical durability is measured under open circuit voltage (OCV) using 50-cm² membrane electrode assemblies that are sub-gasketed to 38-cm² active areas. The electrode is a platinum on carbon slurry coated on the microporous layer of a carbon fiber diffusion media to a 0.4 mg Pt cm$^{-2}$ loadings on both the anode and cathode. The fuel cell, with a serpentine flow-field, is operated at 95° C. and at 50% inlet R.H at a 5/5 stoichiometry of anode and cathode at 0.2 A cm$^{-2}$ equivalent flow and 50 kPa gauge. The OCV is monitored for 200 to 800 hours and the fluoride release rate (FRR) is measured from the analysis of outlet water to determine the percent loss of fluorine versus the total fluorine inventory of the membrane. FIG. 2 provides plots which outline the effect of small amounts of CoTMPP to dramatically improve the OCV durability of fuel cell membranes as compared to a comparative example of Nafion 1000 baseline without the added CoTMPP. The fluoride release rate of the CoTMPP membrane is 10² lower and the degradation rate is reduced.

Figure 3:
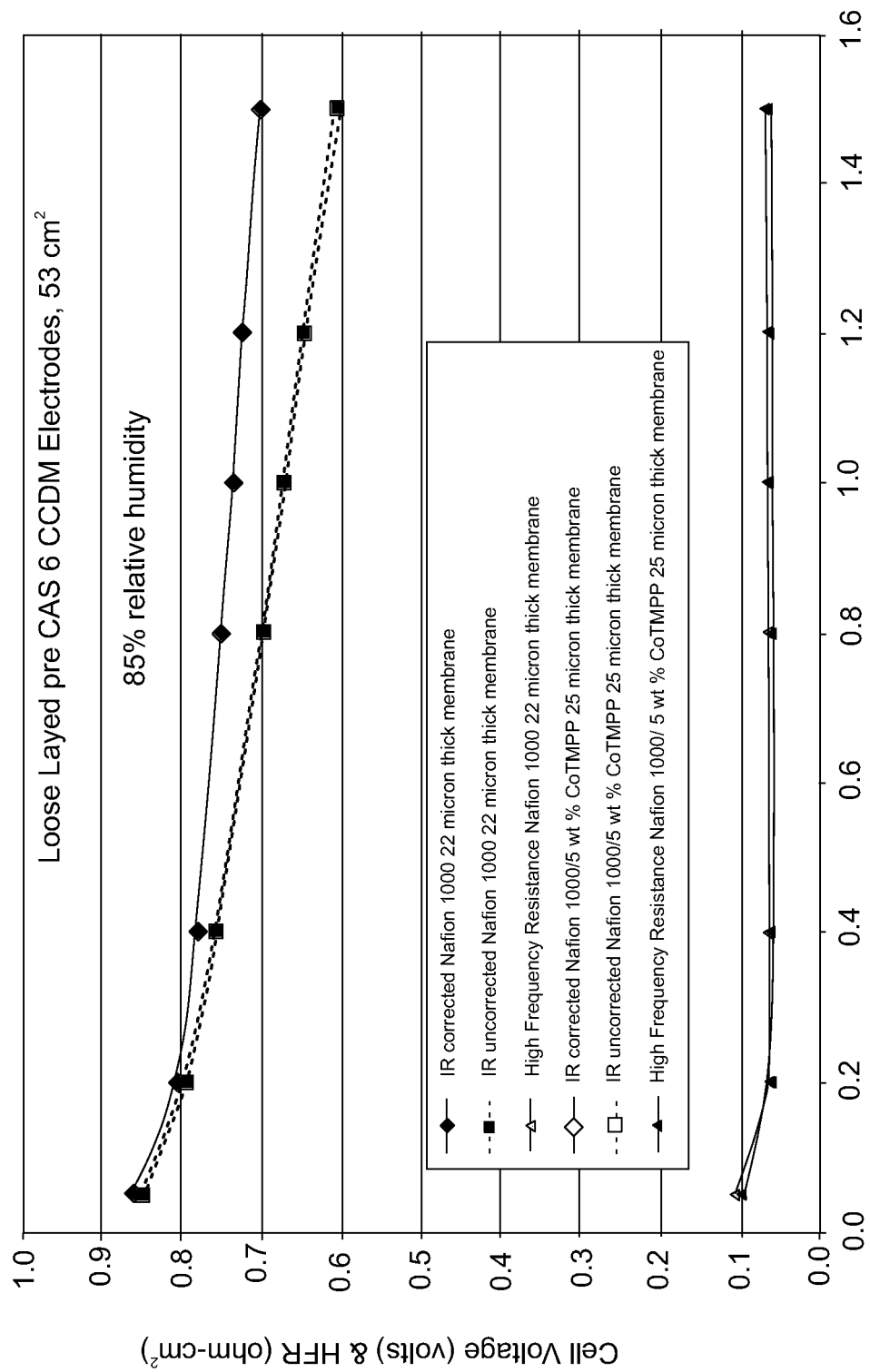
FIG. 3 provides plots of the relative humidity ("RH") sweep profile for Nafion® 1000 with and without Cobalt(II) tetramethoxyphenylporphyrin.

The fuel cell performance is measured using a 50-cm² membrane electrode assemblies prepared by loose laying a catalyst coated diffusion medium with 0.4 mg Pt cm$^{-2}$ loadings on both the anode and cathode. The fuel cell, is operated from 0 to 1.5 A/cm² at 80° C. with 32% inlet R.H at a constant 1.5/2 stoichiometry of anode and cathode at 50 kPa gauge. The addition of CoTMPP to proton exchange membranes does not reduce the in-situ fuel cell performance as shown in FIG. 3 which outlines the achieved fuel cell performance of >0.6 V at 1.5 A/cm² with no change in the high frequency resistance (HFR) of the membrane owing to no losses in membrane resistance.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:
1. An ion conducting membrane for fuel cell applications, the ion conducting membrane comprising:
    an ion conducting polymer comprising a perfluorocyclobutyl moiety; and
    a compound having the following formula:

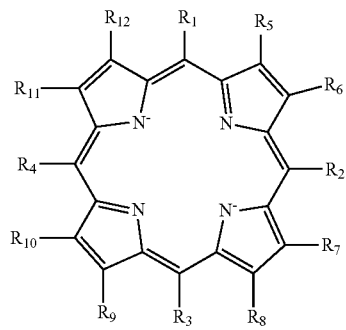

wherein:
$R_1$, $R_2$, $R_3$, $R_4$ are each independently hydrogen, substituted or unsubstituted alkyl or substituted or unsubstituted phenyl wherein the substituted alkyl and the substituted aryl have substitutions with halogens or methoxy or ethoxy; and
$R_5$, $R_6$, $R_7$, $R_8$, $R_9$, $R_{10}$, $R_{11}$, $R_{12}$ are each independently hydrogen.

2. The ion conducting membrane of claim 1 wherein $R_1$, $R_2$, $R_3$, $R_4$, are each phenylmethoxy.

3. An ion conducting membrane for fuel cell applications, the ion conducting membrane comprising:
    an ion conducting polymer comprising a perfluorocyclobutyl moiety; and
    a porphyrin-containing compound having the following formula:

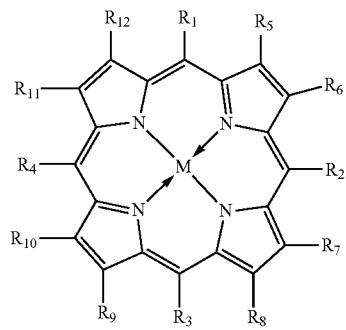

wherein M is $Co^{2+}$, $Co^{3+}$, $Fe^{2+}$, $Fe^{3+}$, $Mg^{1+}$, $Mg^{2+}$, $Mn^{1+}$, $Mn^{2+}$, $Mn^{3+}$, $ClMn^{3+}$, $HOMn^{3+}$, $Cu^{+1}$, $Cu^{2+}$, $Ni^{1+}$, $Ni^{2+}$, $Pd^{1+}$, $Pd^{2+}$, $Ru^{1+}$, $Ru^{2+}$, $Ru^{4+}$, $Vn^{4+}$, $Zn^{1+}$, $Zn^{2+}$, $Al^{3+}$, B, $Si(OH)_2^{2+}$, $Al^{3+}$, $HOIn^{3+}$, $HOIn^{3+}$, $Pb^{2+}$, $Ag^+$, $Sn^{2+}$, $Sn^{4+}$, $Ti^{3+}$, $Ti^{4+}$, $VO^+$, $Pt^{2+}$, $Ce^{3+}$, or $Ce^{4+}$; and
$R_1$, $R_2$, $R_3$, $R_4$ are each independently hydrogen, substituted or unsubstituted alkyl, or substituted or unsubstituted phenyl wherein the substituted alkyl and the substituted aryl have substitutions with halogens or methoxy or ethoxy; and
$R_5$, $R_6$, $R_7$, $R_8$, $R_9$, $R_{10}$, $R_{11}$, $R_{12}$ are each independently hydrogen.

4. The ion conducting membrane of claim 3 wherein the porphyrin-containing compound is Co(II)tetramethoxyphenylporphyrin.

* * * * *